United States Patent
Olson et al.

(10) Patent No.: US 10,021,824 B2
(45) Date of Patent: Jul. 17, 2018

(54) SUPERABSORBENT POLYMER SEED COATINGS AND ASSOCIATED METHODS

(71) Applicant: VJS INVESTMENTS LIMITED, Dubai (AE)

(72) Inventors: Gary Olson, Beaverton, OR (US); John Francis Walsh, Linden, CA (US)

(73) Assignee: VJS INVESTMENTS LIMITED, Dubai (AE)

( * ) Notice: Subject to any disclaimer, the term of this patent is extended or adjusted under 35 U.S.C. 154(b) by 20 days.

(21) Appl. No.: 15/424,060

(22) Filed: Feb. 3, 2017

(65) Prior Publication Data

US 2017/0142894 A1    May 25, 2017

Related U.S. Application Data

(62) Division of application No. 13/281,028, filed on Oct. 25, 2011, now Pat. No. 9,596,801.

(60) Provisional application No. 61/406,353, filed on Oct. 25, 2010.

(51) Int. Cl.
| | |
|---|---|
| A01C 1/06 | (2006.01) |
| A01N 51/00 | (2006.01) |
| A01N 37/36 | (2006.01) |
| A01N 43/653 | (2006.01) |
| C09D 5/14 | (2006.01) |
| C09D 151/02 | (2006.01) |
| C09D 7/61 | (2018.01) |

(52) U.S. Cl.
CPC ............... *A01C 1/06* (2013.01); *A01N 37/36* (2013.01); *A01N 43/653* (2013.01); *A01N 51/00* (2013.01); *C09D 5/14* (2013.01); *C09D 7/61* (2018.01); *C09D 151/02* (2013.01)

(58) Field of Classification Search
CPC ........ A01C 1/06; A01N 37/36; A01N 43/653; A01N 51/00
USPC ....................................................... 504/100
See application file for complete search history.

(56) References Cited

U.S. PATENT DOCUMENTS

| | | |
|---|---|---|
| 3,935,099 A | 1/1976 | Weaver et al. |
| 4,076,663 A | 2/1978 | Masuda et al. |
| 4,093,542 A | 6/1978 | Dahmen et al. |
| 4,113,685 A | 9/1978 | Hubner et al. |
| 4,134,863 A | 1/1979 | Fanta et al. |
| 4,155,888 A | 5/1979 | Mooth |
| 4,323,487 A | 4/1982 | Jones et al. |
| 4,367,297 A | 1/1983 | Hubner et al. |
| 4,408,073 A | 10/1983 | Goossens et al. |
| 4,528,350 A | 7/1985 | Goossens et al. |
| 4,711,919 A | 12/1987 | Peppmoller et al. |
| 4,766,173 A | 8/1988 | Bailey et al. |
| 4,773,967 A | 9/1988 | Peppmoller et al. |
| 4,983,390 A | 1/1991 | Levy |
| 5,118,719 A | 6/1992 | Lind |
| 5,122,544 A | 6/1992 | Bailey et al. |
| 5,147,343 A | 9/1992 | Kellenberger |
| 5,154,713 A | 10/1992 | Lind |
| 5,176,797 A | 1/1993 | Hartan et al. |
| 5,292,404 A | 3/1994 | Hartan et al. |
| 5,350,799 A | 8/1994 | Woodrum et al. |
| 5,512,646 A | 4/1996 | Hartan et al. |
| 5,567,478 A | 10/1996 | Houben et al. |
| 5,821,286 A | 10/1998 | Xu et al. |
| 5,856,370 A | 1/1999 | Chmelir |
| 5,965,149 A | 10/1999 | Silver |
| 6,048,467 A | 4/2000 | Dahmen et al. |
| 6,221,832 B1 | 4/2001 | Casteel et al. |
| 6,228,964 B1 | 5/2001 | Hartan et al. |
| 6,232,285 B1 | 5/2001 | Casteel et al. |
| 6,303,560 B1 | 10/2001 | Hartan et al. |
| 6,660,819 B2 | 12/2003 | Chmelir et al. |
| 6,800,712 B2 | 10/2004 | Doane et al. |
| 7,009,020 B2 | 3/2006 | Doane et al. |
| 7,459,501 B2 | 12/2008 | Doane et al. |
| 8,017,553 B2 | 9/2011 | Doane et al. |
| 2003/0020043 A1 | 1/2003 | Barresi et al. |
| 2004/0068073 A1 | 4/2004 | Doane et al. |
| 2004/0074271 A1 | 4/2004 | Krysiak et al. |
| 2004/0077498 A1* | 4/2004 | Lynch .................. C05G 3/0041 504/100 |
| 2006/0047068 A1 | 3/2006 | Doane et al. |
| 2008/0113866 A1 | 5/2008 | Doane et al. |
| 2008/0236037 A1* | 10/2008 | Rose .................... C09D 197/00 47/57.6 |

OTHER PUBLICATIONS

United States Department of Agriculture, 'Starch-Encapsulated Pesticides', Agricultural Research Service, Nov. 1994, ARS Papers presented at the International Seminar on Research and Development of controlled-Release Formulations of Pesticides—Vienna, Austria, Sep. 6-10, 1993.

Finkenstadt et al., 'Reactive Extrusion of Starch-Polyacrylamide Graft Copolymers: Effects of Monomer/Starch Ratio and Moisture Content', Macromolecular Chemistry and Physics, vol. 206, Issue 16, Published Aug. 19, 2005, pp. 1648-1652.

Athawale et al., 'Recent Trends in Hydrogels Based on Starch-Graft-Acrylic Acid: A Review', Starch/Starke, vol. 53, pp. 7-13, 2001.

Athawale et al., 'Factors Influencing Absorbent Properties of Saponified Starch-g-(acrylic acid-coacrylamide)', Journal of Applied Polymer Science, vol. 77, Issue 11, pp. 2480-2485, 2000.

(Continued)

*Primary Examiner* — Johann R Richter
*Assistant Examiner* — Courtney A Brown
(74) *Attorney, Agent, or Firm* — Merchant & Gould P.C.

(57) ABSTRACT

Superabsorbent polymer products for use in agricultural applications, and methods of making the same, are provided. The superabsorbent polymer is used in a seed coating along with an active ingredient, and optionally a singulating substance, to improve seed germination and/or blooming; improve germination under dry conditions; decrease irrigation requirements; increase propagation, crop growth, and crop production; and improve the efficacy of the active ingredient.

12 Claims, 6 Drawing Sheets

(56) References Cited

OTHER PUBLICATIONS

Zhang et al., 'Perspectives on: Strategies to Fabricate Starch-Based Hydrogels with Potential Biomedical Applications', Journal ofBioactive and Compatible Polymers, vol. 20, No. 3, pp. 297-314, May 2005.
Willett et al., 'Preparation of Starch-Graft-Polyacrylamide Copolymers by Reactive Extrusion', Polymer Engineering and Science, vol. 43, No. 10, pp. 1666-1674, Oct. 2003.
Office Action dated Mar. 19, 2007 for U.S. Appl. No. 11/013,664.
Office Action dated Aug. 8, 2007 for U.S. Appl. No. 11/013,664.
Office Action dated Dec. 5, 2007 for U.S. Appl. No. 11/013,664.
Office Action dated Mar. 19, 2007 for U.S. Appl. No. 11/500,698.
Office Action dated Jan. 11, 2008 for U.S. Appl. No. 11/269,214.
Office Action dated Dec. 5, 2007 for U.S. Appl. No. 11/500,698.
Office Action dated Aug. 2, 2007 for U.S. Appl. No. 11/500,698.
Notice of Abandonment dated May 19, 2008 for U.S. Appl. No. 11/213,563.
Notice of Allowance dated Sep. 19, 2008 for U.S. Appl. No. 12/018,090.
Notice of Allowance dated May 11, 2011 for U.S. Appl. No. 12/264,698.
Office Action dated Sep. 17, 2007 for U.S. Appl. No. 11/269,214.
Office Action dated Jan. 16, 2007 for U.S. Appl. No. 11/269,214.
International Search Report and Publication dated Mar. 9, 2006 for PCT/US2005/30361.
Office Action dated Oct. 22, 2007 for U.S. Appl. No. 11/213,563.
Office Action dated May 9, 2007 for U.S. Appl. No. 11/213,563.
Restriction Requirement dated Mar. 19, 2007 for U.S. Appl. No. 11/213,563.
Office Action dated Aug. 19, 2008 for U.S. Appl. No. 12/018,090.

\* cited by examiner

SUPERABSORBENT POLYMER SEED COATINGS AND ASSOCIATED METHODS

RELATED APPLICATION

The present application is a divisional application of U.S. application Ser. No. 13/281,028, filed on Oct. 25, 2010, which claims priority to U.S. Provisional Application No. 61/406,353, filed on Oct. 25, 2010, and which applications are incorporated herein by reference. To the extent appropriate, a claim of priority is made to each of the above disclosed applications.

TECHNICAL FIELD

The present disclosure relates to seeds that may be coated with one or more superabsorbent polymers; one or more active ingredients to, for example, promote seed growth; and/or one or more singulating substances. The present disclosure further relates to methods of applying these agents to seeds.

DETAILED DESCRIPTION

Superabsorbent polymers include materials that imbibe or absorb at least 10 times their own weight in aqueous fluid and that retain the imbibed or absorbed aqueous fluid under moderate pressure. The imbibed or absorbed aqueous fluid is taken into the molecular structure of the superabsorbent polymer rather than being contained in pores from which the fluid could be eliminated by squeezing. Some superabsorbent polymers can absorb up to 1,500 times their weight in aqueous fluid.

Superabsorbent polymers may have beneficial uses in crop production. For example, a seed coated with a superabsorbent polymer may have a higher rate of germination, have an improved seedling growth rate, and provide water and/or active ingredients during periods of infrequent watering. (As further defined below, "active ingredients" refers to seed treatments other than superabsorbent polymers and/or singulating substances.) Seeds treated with superabsorbent polymers may also inhibit leaching of active ingredients under conditions of excess rainfall or irrigation. Seeds treated with superabsorbent polymers may also be treated with active ingredients such as nutrients, plant growth regulators, insecticides, and fungicides. In some embodiments, seed coatings may be used as carriers for these active ingredients.

As used herein, the terms "treated" and "coated" are to be interpreted broadly, as referring to any application of an agent (i.e., a superabsorbent polymer or other seed treatment) to a seed. "Treating" or "coating" a seed or seeds does not require that the agent be uniformly distributed on the surface of the seed or seeds; nor do these terms require the entire surface of the seed to be covered.

Due to the chemical nature of superabsorbent polymers, they may quickly hydrate with water during the process of treating seeds, thus forming a sticky, gelatinous material that may make it difficult to uniformly apply the superabsorbent polymer to the seeds. Further, the treated seeds may become tacky and, on drying, form aggregates that are unsuitable for further use.

This issue can be addressed by adding a substantial quantity of inert powders or a combination of inert powders and fertilizer powders to the seeds in a coating process commonly referred to as a build-up coating. The superabsorbent polymer may be incorporated into the build-up coating during the build-up coating process. The build-up process may use a binder to incorporate the powder materials onto the seed. Build-up coatings typically comprise 34% to 300% or more of the finished coated seed weight. The build-up process mitigates the difficulties of applying superabsorbent polymers to seeds; however, it may be expensive and may only be suitable to limited types of seeds, such as turf grasses, alfalfa, clovers, and some vegetables. For many other seed types, however, the use of a build-up coating is unacceptable or not practical. Unsuitable seed types may include many field crops planted on large acreage, such as corn, wheat, soybeans, cotton, sunflowers, and so on.

The present disclosure provides a method for treating seeds with superabsorbent polymers without the need to use a build-up coating. This method may not require the use of a separate binder or adhesive compound or solution.

The use of a singulating substance in the superabsorbent polymer seed treatment may alleviate the seed clumping problem and allow the treated seeds to separate from each other. As used herein, the term "singulating substance" refers to any substance that assists the seeds in separating one from another while the seeds are substantially wet. One exemplary embodiment of a singulating substance is talc. Other dry solid powders may be used as singulating substances. Examples of dry solids include calcium carbonate, sodium sulfate, mica, magnesium sulfate, wood flour, and silica. In some embodiments, a singulating substance may be comprised of combinations or blends of one or more of these exemplary substances or their equivalents.

The quantity of singulating substance used in treating seeds may be quantified by its relationship to the weight of raw seeds that are being coated. For example, the amount of the singulating substance used may be between about 0.2% and about 0.3% of the weight of the seeds. More or less singulating substance may also be suitable depending on seed type, seed moisture levels, and the active ingredients used. For example, the weight of the singulating substance as a percentage of the weight of the seeds may be 0%, at least 0.1%, between about 0.05% and about 0.75%, between about 0.05% and about 1%, or below about 1.5%. Additionally, the amount of singulating substance as a percentage of seed weight may be from about 0.05% to about 0.50%, including ranges from about 0.075% to about 0.30% and from about 0.20% to about 0.30%. Any of the amounts herein disclosed are relevant for use with any seed type. Without being bound by theory, it is believed that the singulating substance acts as a slip agent to increase the flowability and reduce tackiness of the coated seeds.

The amount of additive (i.e., singulating substance, superabsorbent polymer, active ingredient, etc.) used may be expressed as a "rate" in some instances. As used herein, a substance added at a rate of X % refers to an amount of substance equal to X % of the weight of the seeds to be treated. So, for example, singulating substance added at a rate of 0.20% means that the amount of singulating substance added (by weight) is 0.20% of the weight of the seeds to be treated.

The amount of superabsorbent polymer used may also be related to the weight of raw seeds that are to be coated. For example, the amount of superabsorbent polymer used may range from about 0.25% to about 1.0% of the weight of the seeds. The amount of superabsorbent polymer may be higher or lower than this depending on, for example, seed type and the treating equipment used. In some embodiments, the weight of superabsorbent polymer as a percentage of the weight of the seeds may be at least 0.1%, between about 0.1% and about 1%, between about 0.2% and about 0.5%, up to about 0.6%, or no more than about 1.5%. The types of seeds coated may include corn, soybeans, wheat, cotton, sorghum, sunflowers, canola, vegetables, barley, oats and other small grains, dry beans, peas, lentils, and peanuts. One exemplary proportion of superabsorbent polymer for soybean seeds may be between about 0.20% and about 0.50%, including proportions between about 0.25% and about 0.35%. In some embodiments these proportions may also be used in connection with similarly sized seeds such as corn, cotton, and so on. Furthermore, an exemplary proportion of superabsorbent polymer for corn seeds may be between about 0.25% and about 1.0%. Additionally, an exemplary proportion of superabsorbent polymer for wheat seeds may be between about 0.5% and about 1.5%, including proportions between about 0.5% and about 1.0%. Notwithstanding these specific examples, any amount or proportion of superabsorbent polymer disclosed herein may be used in connection with any type of seed.

In certain embodiments, the superabsorbent polymer used is a starch graft copolymer. In one particular embodiment, the superabsorbent polymer used is a starch-g-poly (2-propenamide-co-2-propenoic acid) potassium salt starch graft copolymer sold under the trademark Zeba by Absorbent Technologies, Inc.

A superabsorbent polymer, such as a cross-linked starch graft copolymer, may be used in various particle sizes prior to coating the seed, depending on the specific agricultural application intended. Synthetic superabsorbent polymers including polyacrylamides and polyacrylates may be used. For example, the superabsorbent polymer may have a particle size finer than about 200 mesh. Alternatively, the particle size may be between about 200 mesh and about 400 mesh. The particle size may also be finer than 100 mesh.

The amount of active ingredient used may also be related to the weight of raw seeds that are being coated. The active ingredient used may be, for example, a fertilizer, an insecticide, a fungicide, a nutrient or plant growth regulator, an herbicide, or a biological material, or combinations thereof. It should be recognized that the relative amount of active ingredient used may vary depending on the type of active ingredient used. The amount of active ingredient used, as a percentage of the weight of seeds to be treated, may range from about 0.01% to about 50%. For example, the amount of active ingredient for insecticides and fungicides for treating corn, soybeans, wheat, oats and other small grains, dry beans, peas, lentils, and peanuts may be between about 0.01% and about 3.0% of the weight of the seeds. When using fertilizer as an active ingredient, the amount of active ingredient may range from about 1% to about 50% of the weight of the seeds. In one embodiment, the active ingredient used may be a combination of an insecticide and a fungicide manufactured by Syngenta Crop Protection Inc. of Greensboro, N.C., under the trademark Cruiser Maxx. In another embodiment, the active ingredient used may be a fungicide manufactured by Syngenta Crop Protection Inc. of Greensboro, N.C., under the trademark Dividend Extreme.

Notwithstanding these specific examples, use of any active ingredient, alone or in combination with other active ingredients, in any of the relative amounts outlined herein is within the scope of the current disclosure.

Examples of biological materials (living organisms such as bacteria and fungi) which may be used as active ingredients include, bacteria of the genera *Rhizobium, Bacillus, Pseudomonas, Azospirillum,* and *Serratia*; fungi of the genera *Trichoderma, Glomus, Beauveria, Gliocladium,* and *Penicillium*; and mycorrhizal fungi.

Exemplary plant growth-enhancing active ingredients include fertilizers, pesticides, and soil-based nutrients, all of which may be in solid, crystalline, aqueous, or liquid form. A list of exemplary pesticides includes acaricides, algicides, antifeedants, avicides, bactericides, bird repellents, chemosterilants, fungicides, herbicide safeners, insect attractants, insect repellents, mammal repellents, molluscicides, nematicides, plant activators, plant growth regulators, rodenticides, synergists, and virucides. A combination and/or blend of these plant growth enhancers may be used.

Exemplary insecticide-type active ingredients include thiodan, diazinon, malathion, imidacloprid, clothianidin, thiamethoxam, thiodicarb, beta-cyfluthrin, and abamectin, as well as Poncho Beta™ (active ingredients=clothianidin and beta-cyfluthrin), manufactured by Bayer Crop Science of Research Triangle Park, N.C., and Aeris™ (active ingredients=thiodicarb and imidacloprid), manufactured by Bayer Crop Science of Research Triangle Park, N.C. Exemplary fungicides include captan, thiram, metalaxyl, ipconazole, triticonazole, prothioconazole, flutolanil, myclobutanil, triadimenol, pyraclostrobin, boscalid, aluminum tris (o-ethylphosphenate), iprodione, kresoxim-methyl, trifloxystrobin, mefenoxam, methoxyacetylamino-(R)-2-2[2,6-dimethylphenyl-propionic acid methyl ester], difenoconazole, chlorothalonil, carboxin, fludioxonil, azoxystrobin, and tebuconazole, as well as Proceed™ (active ingredients=prothioconazole, tebuconazole, and metalaxyl), manufactured by Bayer Crop Science of Research Triangle Park, N.C.; Trilex Advanced™ (active ingredients=trifloxystrobin, triadimenol, and metalaxyl), manufactured by Bayer Crop Science of Research Triangle Park, N.C.; Vitaflo-280™ (active ingredients=carboxin and thiram), manufactured by Chemtura AgroSolutions of Laurenceville, Ga.; and Coronet™ (active ingredients=boscalid and pyraclostrobin), manufactured by Bayer Crop Protection of Research Triangle Park, N.C. In one embodiment, a dual fungicide manufactured by Syngenta Crop Protection Inc. of Greensboro, N.C., under the trademark Dividend Extreme (active ingredients=difenoconazole and mefenoxam) may be used. A combination or blend of these insecticides and fungicides may be used. For example, a combination of an insecticide and a fungicide manufactured by Syngenta Crop Protection Inc. of Greensboro, N.C., under the trademark Cruiser Maxx (active ingredients=thiamethoxam, mefenoxam, and difenoconazole) may be used.

A list of exemplary soil-based nutrients that may be used as active ingredients includes calcium, magnesium, potassium, phosphorus, boron, zinc, manganese, copper, iron, sulfur, nitrogen, molybdenum, and fish meal. A combination or blend of these soil-based nutrients may be used.

In some embodiments, seeds may be treated with one or more of an active ingredient, a superabsorbent polymer, and/or a singulating substance by using a commercial rotary coating machine and manually adding liquid and powder ingredients. The liquids may be injected onto a spinning disk applicator using a syringe. Powders may be added to the seed mass via a funnel with a delivery tube from the bottom of the funnel to an area just above the seed mass. For larger rotary coaters, the liquids and powders may be added using automated pumps and powder feeders.

Seeds may be added to the coating chamber and spun in the rotary coating machine. In some embodiments, the active ingredient may be added to the seed first. In one embodiment, the addition of the active ingredient may be completed prior to the addition of a superabsorbent polymer. The active ingredient and the superabsorbent polymer may then be followed by the addition of a singulating substance. The seeds may further be spun for a few additional seconds and then discharged from the machine.

In an exemplary test run, visual analysis of seeds treated with an active ingredient, a superabsorbent polymer, and a singulating substance suggested the active ingredient and the superabsorbent polymer were uniformly distributed on the seeds. Further, in the same test run, the seeds were generally well singulated and not tacky to the touch. In contrast, seeds treated only with an active ingredient and a superabsorbent polymer, without a singulating substance, were quite tacky and clumped together.

In certain embodiments, the singulating substance may be added immediately after the addition of the superabsorbent polymer and active ingredient. For example, it may be added within 2 seconds of the active ingredient and superabsorbent polymer. In other embodiments, the singulating substance may be added within 5 seconds of the active ingredient and superabsorbent polymer. Alternatively, in other embodiments, the singulating substance may be added less than 10 seconds after the active ingredient and superabsorbent polymer.

The types of superabsorbent polymers for use in agricultural applications may include those made by graft polymerizing a monomer onto a starch in the presence of an initiator to form a starch graft copolymer, cross-linking the starch graft copolymer, adjusting the pH of the cross-linked starch graft copolymer such as by neutralization, and isolating and drying the cross-linked starch graft copolymer. Alternatively, synthetic superabsorbent polymers, including polyacrylamides and polyacrylates, may be used.

Exemplary monomers for use in the above-described superabsorbent polymers may include acrylonitrile, acrylic acid, and/or methacrylic acid. Exemplary monomers may further include acrylamide or methacrylamide. Sulfonic acids, such as 2-acrylamido-2-methyl-propanesulfonic acid (AMPS) and vinyl sulfonic acid may also be used. Moreover, acrylates, such as ethyl acrylate and potassium acrylate may be used. Additionally, derivatives and mixtures of the above-listed monomers are also within the scope of this disclosure.

Exemplary methods of forming starch graft copolymer superabsorbent polymers are described in U.S. Pat. Nos. 6,800,712 and 7,423,090, which are incorporated herein by reference.

The agricultural application of seeds treated with an active ingredient and superabsorbent polymers, as described above, may result in earlier seed germination, improved germination under dry conditions, decreased irrigation requirements, increased propagation, increased crop growth, increased crop production, and/or improved efficacy of the active ingredient, as the active ingredient is held to the seed longer than without a seed coating, which may be particularly useful for a water-soluble active ingredient. Thus, the treatment of seeds with an active ingredient and a superabsorbent polymer, as discussed herein, may be used in agricultural applications.

Those skilled in the art, having the benefit of this disclosure, will recognize that the methods and compositions disclosed herein may be practiced without one or more of the specific details described, or with other methods, components, materials, etc. In some cases, well-known materials, components, or method steps are not shown or described in detail. Furthermore, the described method steps, compositions, etc., may be combined in any suitable manner in one or more embodiments. It will also be readily understood that the methods and compositions of the embodiments as generally described herein could be arranged and designed in a wide variety of different configurations.

The order of the steps or actions of the methods described in connection with the embodiments disclosed may be changed as would be apparent to those skilled in the art having the benefit of this disclosure. Thus, any order in the detailed description is for illustrative purposes only and is not meant to imply a required order.

The following examples demonstrate exemplary procedures used to treat seeds with an active ingredient and a superabsorbent polymer using the methods described herein.

General Seed Treatment Procedure

A Cimbria Heid CentriCoater CC lab model rotary coating machine was used for the following examples. The batch size of the seeds used was at least 1 pound, depending on the seed type. The rotor speed was 30-40 rpm. For the addition of small quantities of liquid and powder to the seed mass, the material was added manually. The liquids were premeasured and injected onto a spinning disk applicator using a syringe. A syringe with extra air volume was used in order to chase the liquid completely through the delivery tube to the spinning disk. Powders were added to the seed mass via a funnel with a delivery tube from the bottom of the funnel to an area just above the seed mass. Shaking the funnel as the powders were added prevented the powders from sticking to the funnel or the delivery tube. In other examples, which may utilize larger rotary coaters, the liquids and powders may be added using automated pumps and powder feeders.

In the following examples, the seeds were first added to the coating chamber spun in the rotary coating machine. Second, the active ingredient was added to the seeds. When the addition of the active ingredient was completed, a superabsorbent polymer was added next. Immediately following the superabsorbent polymer addition, talc was added. Talc was added within 2 seconds of adding the superabsorbent polymer in order for the talc to act as a slip agent to increase the seed flowability and to reduce tackiness of the coated seeds. When all the coating materials were added, the seeds were spun for a few additional seconds and then discharged from the coating machine. In other applications, the quantities of each component may vary depending on the equipment used.

EXAMPLE 1

Using the general procedure described above, soybean seeds were treated with the active ingredient Cruiser Maxx, manufactured by Syngenta Crop Protection Inc. as a combination insecticide and fungicide, and the superabsorbent polymer starch-g-poly (2-propenamide-co-2-propenoic acid) potassium salt starch graft copolymer (sold under the trademark Zeba by Absorbent Technologies, Inc.). The active ingredient was applied at a rate of 3 fluid ounces per 100 pounds of soybean seeds, or approximately 0.84 milliliters (ml) per pound of seed. The active ingredient was added as a pre-mix with water at a 1:2 ratio. For example, 0.84 ml Cruiser Maxx+1.68 ml water=2.52 ml pre-mix. The rotor speed was 40 rpm. The quantities of each component used in this example were: 454 grams (g) soybean seed; 2.52 ml Cruiser Maxx/water pre-mix; 1.135 g Zeba (0.25% of seed weight); and 0.91 g talc (0.2% of seed weight).

After coating, the seeds singulated easily and were not tacky. The active ingredient and the superabsorbent polymer appeared to be uniformly distributed on the seeds by visual inspection. These soybeans were planted and analyzed, as shown in FIGS. 1-5, and as discussed below.

EXAMPLE 2

Using the general procedure described above, hybrid corn seeds were treated with the active ingredient Cruiser Maxx, manufactured by Syngenta Crop Protection Inc. as a combination insecticide and fungicide, and the superabsorbent polymer starch-g-poly (2-propenamide-co-2-propenoic acid) potassium salt starch graft copolymer (sold under the trademark Zeba by Absorbent Technologies, Inc.). The active ingredient was applied at a rate of 2.3 fluid ounces per 100 pounds of corn seed, or approximately 0.644 ml per pound of seed. The active ingredient was added as a pre-mix with water at a ratio of 0.644 ml Cruiser Maxx+4.66 ml water=5.304 ml pre-mix. The rotor speed was 40 rpm. The quantities of each component used in this example were: 454 g corn seed; 5.304 ml Cruiser Maxx/water pre-mix; 1.159 g Zeba (0.25% of seed weight); and 0.91 g talc (0.2% of seed weight).

After coating, the seeds singulated easily and were not tacky. The active ingredient and the superabsorbent polymer appeared, by visual inspection, to be uniformly distributed on the seeds.

EXAMPLE 3

Again, using the general procedure described above, hybrid corn seeds were treated with the active ingredient Cruiser Maxx, manufactured by Syngenta Crop Protection Inc. as a combination insecticide and fungicide, and the superabsorbent polymer starch-g-poly (2-propenamide-co-2-propenoic acid) potassium salt starch graft copolymer (sold under the trademark Zeba by Absorbent Technologies, Inc.). The active ingredient was used at a rate of 4.6 fluid ounces per 100 pounds of corn seed, or approximately 1.29 ml per pound of seed. The active ingredient was added as a pre-mix with water at a ratio of 1.29 ml Cruiser Maxx+4.01 ml water=5.3 ml pre-mix. The rotor speed was 40 rpm. The quantities of each component used in this example were: 454 g corn seed; 5.3 ml Cruiser Maxx/water pre-mix; 1.59 g Zeba (0.35% of seed weight); and 0.91 g talc (0.2% of seed weight).

After coating, the seeds singulated easily and were not tacky. The active ingredient and the superabsorbent polymer appeared to be uniformly distributed on the seeds by visual inspection.

EXAMPLE 4

Using the general procedure described above, wheat seeds were treated with the active ingredient Dividend Extreme, manufactured by Syngenta Crop Protection Inc. as a fungicide, and the superabsorbent polymer starch-g-poly (2-propenamide-co-2-propenoic acid) potassium salt starch graft copolymer (sold under the trademark Zeba by Absorbent Technologies, Inc.). The active ingredient was applied at a rate of 2 fluid ounces per 100 pounds of wheat seed in all trials, or approximately 0.56 ml per pound of seed. The active ingredient was added as a pre-mix with water at a ratio of 0.56 ml Dividend Extreme+4.48 ml water=5.04 ml pre-mix. The rotor speed was 40 rpm. The seed load was 681 g per batch. The quantities of each component used in this example were: 681 g wheat seed; 7.56 ml Dividend Extreme/water pre-mix; 3.4 g Zeba (0.5% of seed weight); and 1.35 g talc (0.2% of seed weight).

After coating, the seeds singulated easily and were not tacky. The active ingredient and the superabsorbent polymer appeared to be uniformly distributed on the seeds by visual inspection.

Figure 6:
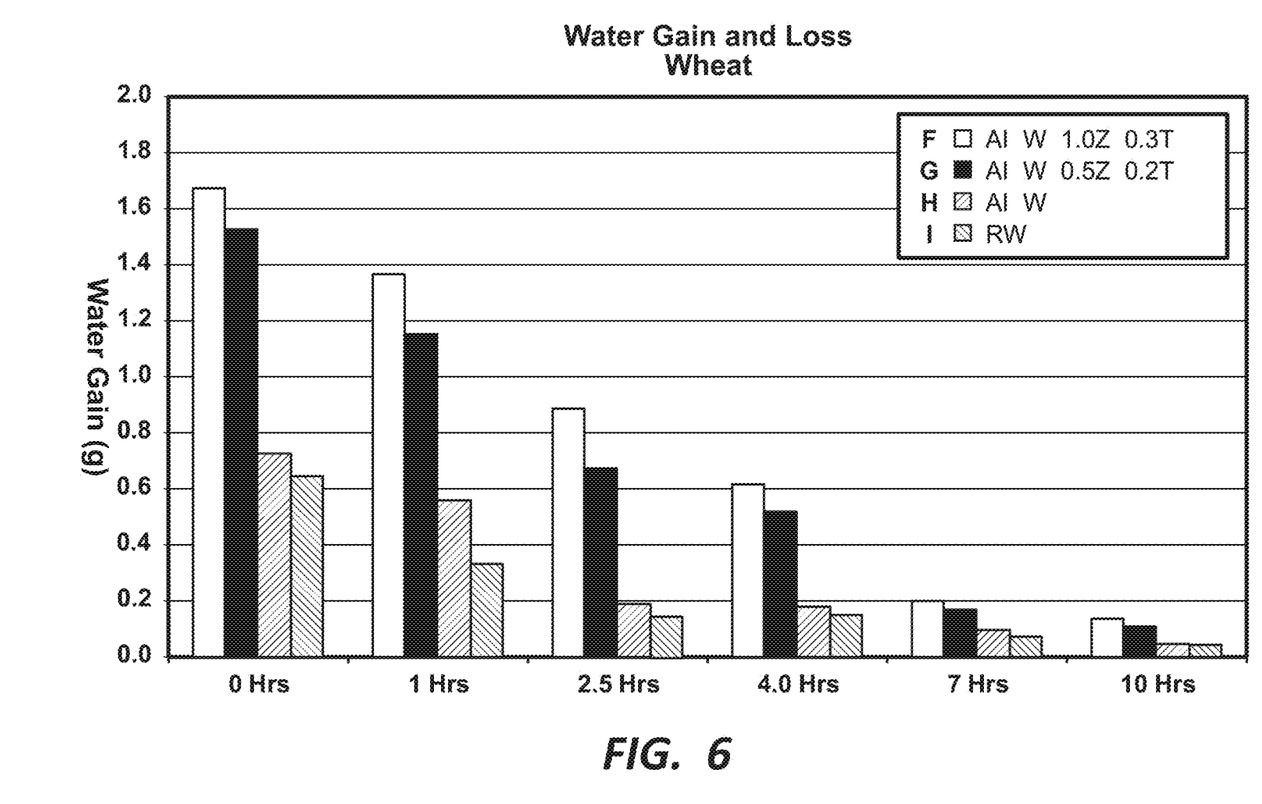
FIG. 6 is a graph comparing the amount of water gain and loss by wheat seeds when not coated; when coated with an active ingredient; and when coated with an active ingredient, a superabsorbent polymer, and a singulating substance.

These wheat seeds were analyzed as shown in FIG. 6, and as discussed below.

Experimental Comparison

The effectiveness of the superabsorbent polymer product formed using the methods described herein, as exemplified by Examples 1 and 4, was tested and analyzed in comparison to various alternative seed coatings containing varying components and in comparison to control subjects, as further described below.

Figure 1:
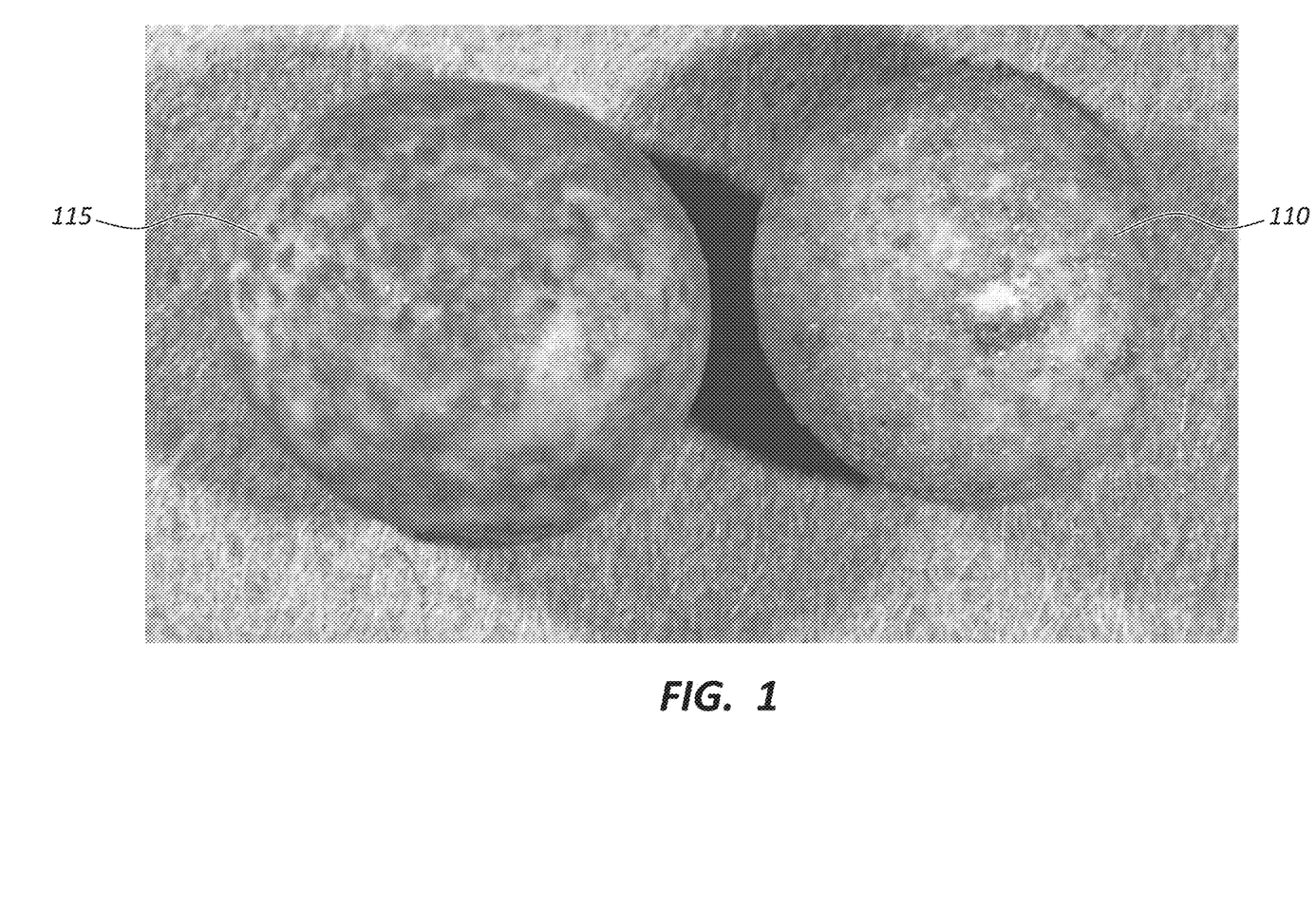
FIG. 1 is a photograph of one soybean seed coated with an active ingredient and one soybean seed coated with a superabsorbent polymer, an active ingredient, and a singulating substance.

FIG. 1 is a photograph of one soybean seed 115 coated with Cruiser Maxx at a rate of 3 fluid ounces per hundredweight, and one soybean seed 110 coated with Cruiser Maxx at a rate of 3 fluid ounces per hundredweight, a starch-g-poly (2-propenamide-co-2-propenoic acid) potassium salt starch graft copolymer at a rate of 0.35% of seed weight, and talc at a rate of 0.2% of seed weight. Thus, seed 115 is only coated with an active ingredient while seed 110 is coated with an active ingredient, a superabsorbent polymer, and a singulating substance.

Figure 2:
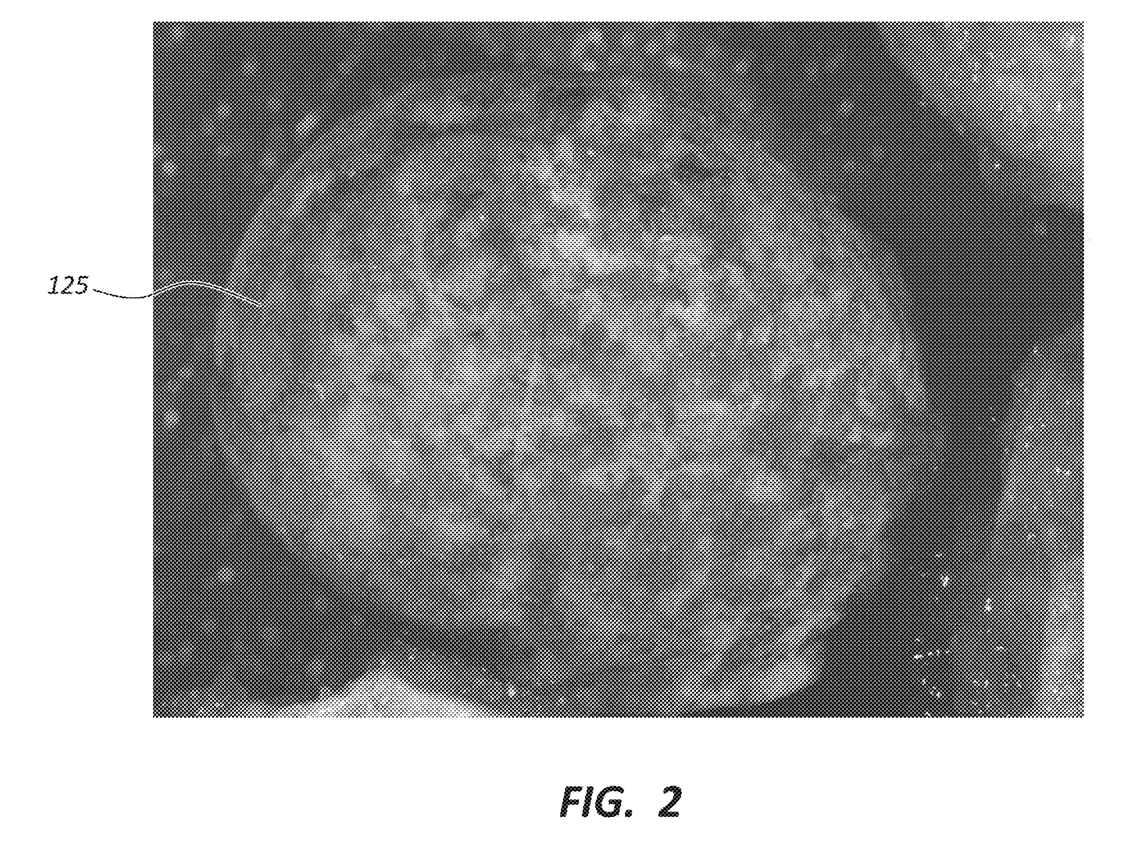
FIG. 2 is a photograph of a soybean seed coated with an active ingredient and treated with water.
Figure 3:
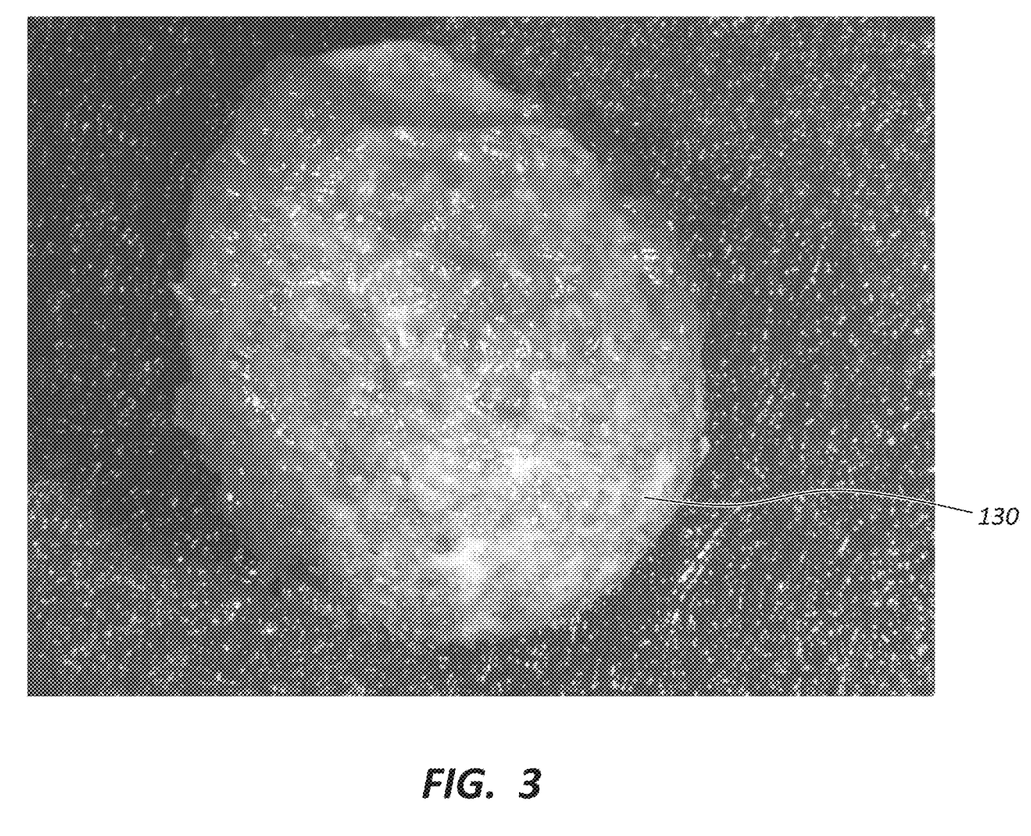
FIG. 3 is a photograph of a soybean seed coated with an active ingredient and a superabsorbent polymer, and treated with water.

FIG. 2 is a photograph of a soybean seed 125 coated with Cruiser Maxx at a rate of 3 fluid ounces per hundredweight and treated with 0.25-0.33 ml of water per seed. As shown in the photograph, there is little or no gel formation around the seed 125. In contrast, FIG. 3 is a photograph of a soybean seed 130 coated with Cruiser Maxx (3 fluid ounces per hundredweight), a starch-g-poly (2-propenamide-co-2-propenoic acid) potassium salt starch graft copolymer (0.35% of seed weight), and talc (0.2% of seed weight), then treated with 0.25-0.33 ml of water per seed. The seed 130 coat containing the superabsorbent polymer shows evidence of gel formation.

Figure 4:
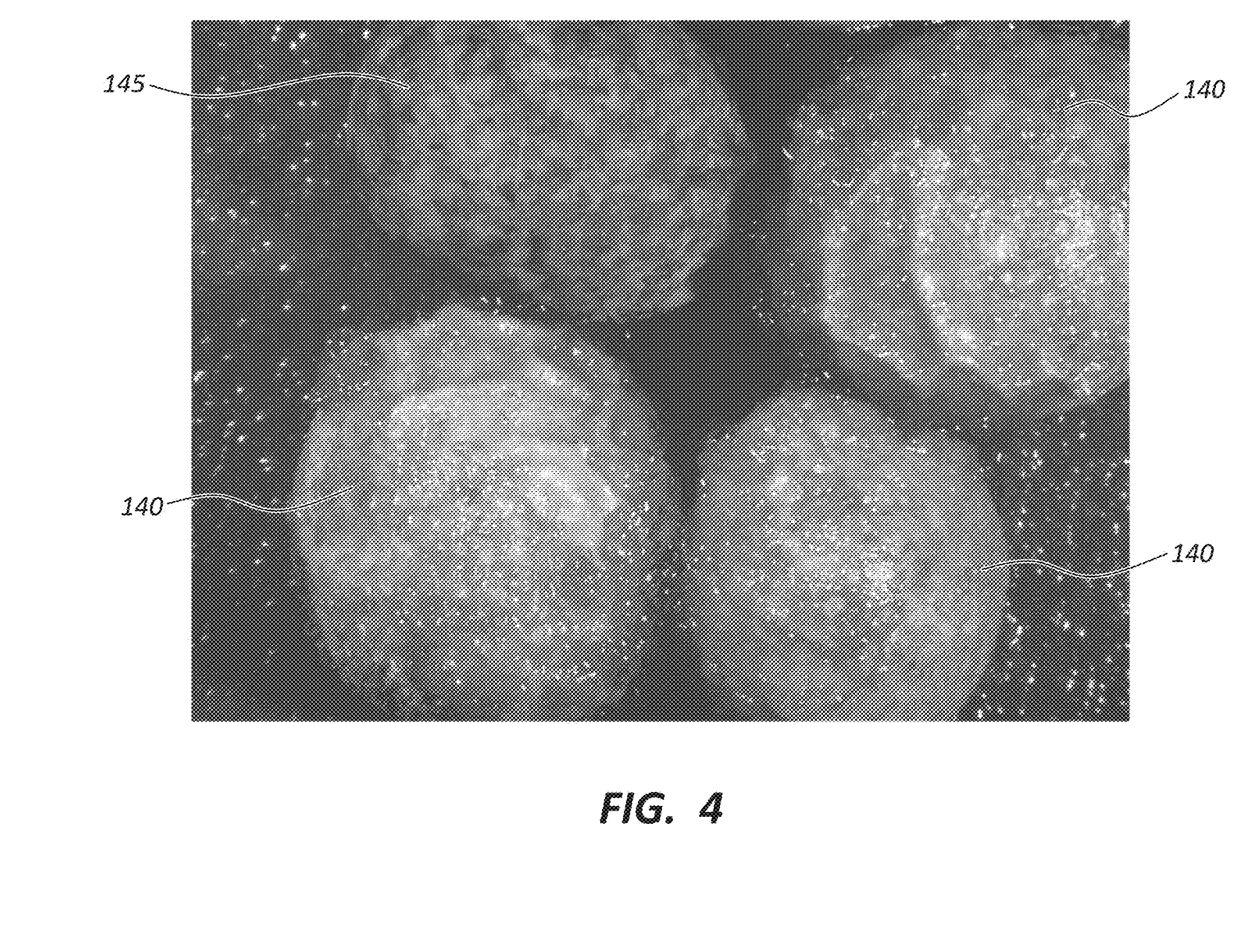
FIG. 4 is a photograph of one soybean seed coated with an active ingredient and three soybean seeds coated with an active ingredient and a superabsorbent polymer; all the seeds have been treated with water.

FIG. 4 is a photograph comparing one soybean seed 145 treated only with Cruiser Maxx (3 fluid ounces per hundredweight), with three soybean seeds 140 coated with Cruiser Maxx (3 fluid ounces per hundredweight), a starch-g-poly (2-propenamide-co-2-propenoic acid) potassium salt starch graft copolymer (0.35% of seed weight), and talc (0.2% of seed weight). All seeds were treated with 0.25-0.33 ml of water per seed. The seed 140 coats that contain the superabsorbent polymer show evidence of gel formation.

Figure 5:
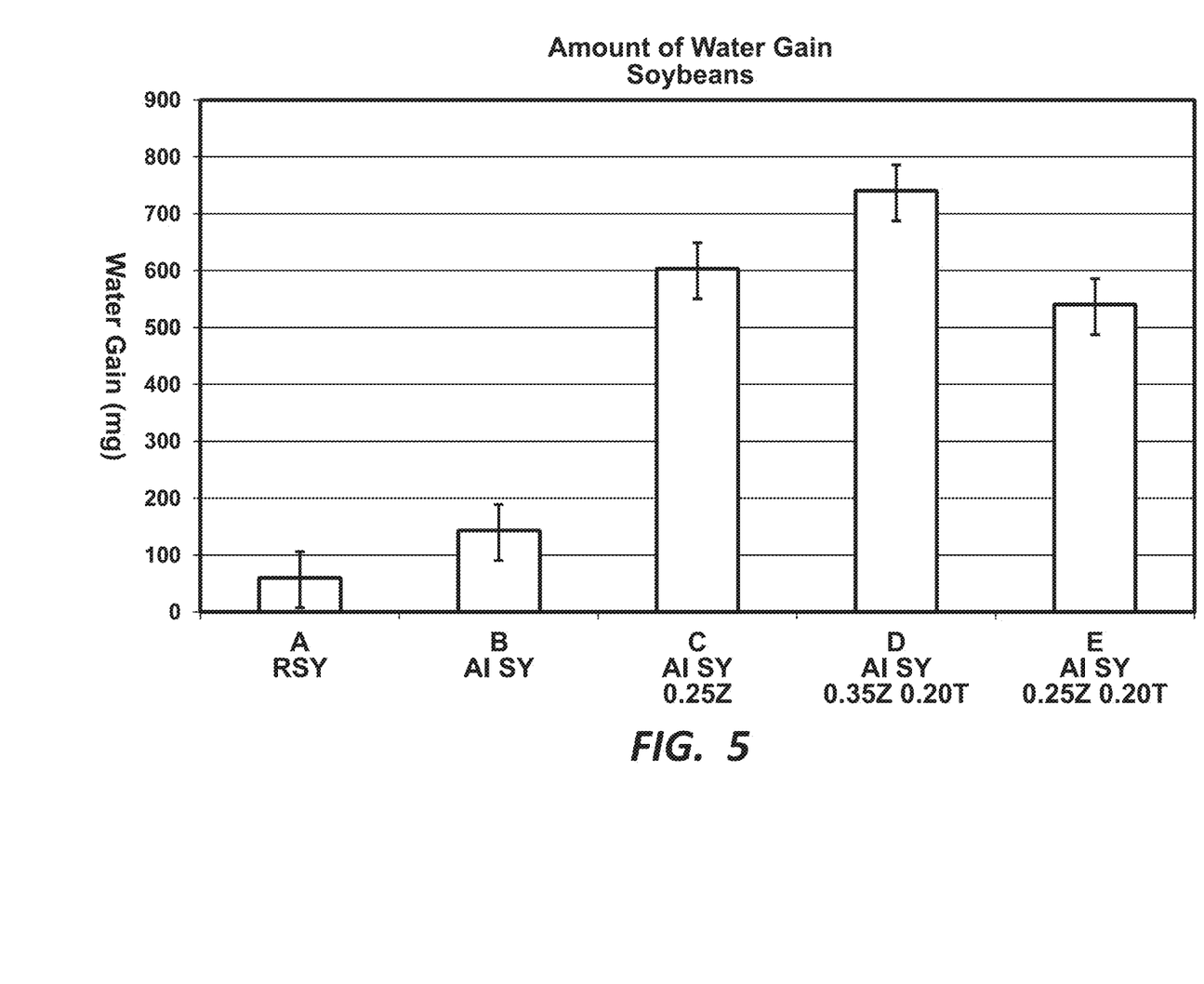
FIG. 5 is a graph comparing the amount of water gain by soybean seeds when not coated; when coated with an active ingredient; when coated with an active ingredient and a superabsorbent polymer; and when coated with an active ingredient, a superabsorbent polymer, and a singulating substance.

FIG. 5 is a graph comparing the amount of water gain in milligrams after a single saturation event. As referenced in this Figure, a "single saturation event" comprises treating an equal number of seeds with drops of water from a syringe, allowing the seeds to stand for 5 minutes, and draining the excess water via gravity at an angle of 45 degrees. In the test example from which FIG. 5 was generated, the saturation was conducted on a stainless-steel fine mesh screen at ambient lab conditions of temperature and relative humidity. The graph of FIG. 5 compares soybean seeds after a single saturation event when the seeds are not coated (labeled as "A" or RSY—raw soy beans—on the X-axis); soybean seeds coated with Cruiser Maxx at a rate of 3 fluid ounces per hundredweight (labeled as "B" or AI SY—active ingredient, soybeans—on the X-axis); soybean seeds coated with Cruiser Maxx at a rate of 3 fluid ounces per hundredweight and a starch-g-poly (2-propenamide-co-2-propenoic acid) potassium salt starch graft copolymer at a 0.25% rate (labeled as "C" or AI SY 0.25Z—active ingredient, soybeans, 0.25% Zeba—on the X-axis); soybean seeds coated with Cruiser Maxx at a rate of 3 fluid ounces per hundredweight, a starch-g-poly (2-propenamide-co-2-propenoic acid) potassium salt starch graft copolymer at a 0.35% rate, and talc at a 0.2% rate (labeled as "D" or AI SY 0.35Z 0.20T—active ingredient, soybeans, 0.35% Zeba, 0.20% talc—on the X-axis); and soybean seeds coated with Cruiser Maxx at a rate of 3 fluid ounces per hundredweight, a starch-g-poly (2-propenamide-co-2-propenoic acid) potassium salt starch graft copolymer at a 0.25% rate, and talc at a 0.2% rate (labeled as "E" or AI SY 0.25Z 0.20T—active ingredient, soybeans, 0.25% Zeba, 0.20% talc—on the X-axis).

As shown in FIG. 5, the amount of water gain for the soybean seeds coated with the superabsorbent polymer and the active ingredient (C, D, and E) is significantly higher than the amount of water gain for soybean seeds coated with the active ingredient alone (B). Also, as shown by comparing bar C to bar E, the presence of talc as a singulating substance has little to no effect (within error) on the amount of water gain by the seeds.

Soybean seeds treated as described in FIG. 5 (i.e., A—RSY; B—AI SY; C—AI SY 0.25Z; D—AI SY 0.35Z 0.20T; and E—AI SY 0.25Z 0.20 T) were planted in a field plot on day 1 of a study, with a row length of 20 feet and a spacing between the rows of 6-8 inches. The seeds were planted at a depth of about 1.5 inches and a spacing of about 3 inches, with a single-row mechanical planter. The soil was moist at planting. The plot was irrigated nine and 21 days after planting. The air temperature for the duration of the study averaged 87° F. for daytime highs and 51° F. for nighttime lows. The seedlings were harvested at day 23. The results of this experiment are further described below.

Ten days after planting, rows of the soybeans corresponding to groups D and E—that is, those groups treated with talc in addition to an active ingredient and a superabsorbent polymer—appeared to have more plants than rows corresponding to group C, the row treated only with an active ingredient and a superabsorbent polymer. Additionally, 20 days after planting, rows D and E also appeared to have more plants, and the plants generally appeared larger, than the plants of row C.

The following table shows percentage germination of seeds corresponding to each group (A, B, C, D, E) two, three, four, and five days after planting. Here, and in other tables included below, the lowercase letters signify statistical significance; values marked with identical letters have no statistically significant variation from values within the same column, while those marked with different letters do show statistically significant variation.

| Group | Days from Planting | | | |
|---|---|---|---|---|
| | 2 | 3 | 4 | 5 |
| A - RSY | 0.0 a | 25.0 b | 85.4 b | 95.8 a |
| B - AI SY | 0.0 a | 20.8 b | 85.4 b | 97.9 a |
| C - AI SY 0.25Z | 0.0 a | 52.1 a | 100.0 a | 100.0 a |
| D - AI SY 0.35Z 0.20T | 0.0 a | 77.1 a | 100.0 a | 100.0 a |
| E - AI SY 0.25Z 0.20T | 0.0 a | 52.1 a | 100.0 a | 100.0 a |

As reflected in this table, seeds treated with a superabsorbent polymer (groups C, D, E) germinated more quickly than seeds that were not so treated, showing a statistically significant difference in germination on days 3 and 4 after planting. Furthermore, the groups treated with a superabsorbent polymer showed a significant increase in primary root weight after six days, compared to the seeds not treated with a superabsorbent polymer, as shown in the table below, which records the average primary root weight, in grams, of the test groups six days after planting.

| Group | Days from Planting |
|---|---|
| | 6 |
| A - RSY | 0.030 c |
| B - AI SY | 0.033 bc |
| C - AI SY 0.25Z | 0.038 ab |
| D - AI SY 0.35Z 0.20T | 0.040 a |
| E - AI SY 0.25Z 0.20T | 0.037 ab |

The next table shows values for six parameters of soybean plants from each group (A, B, C, D, E) which were removed from the plot and frozen 14 days after planting. The six parameters are (1) quality, a visual assessment based on a scale of 1-9; (2) root length in centimeters; (3) top length in centimeters; (4) total length in centimeters; (5) dry weight of the seedling in grams; and (6) dry weight of the root in grams. Again, the lowercase letters indicate statistically significant variation within columns.

| Group/ Parameter | Quality (1-9) | Root Length (cm) | Top Length (cm) | Total Length (cm) | Seedling Weight (g) | Root Weight (g) |
|---|---|---|---|---|---|---|
| A - RSY | 6.33 b | 7.23 b | 9.57 a | 16.8 b | 0.16 a | 0.12 a |
| B - AI SY | 3.33 d | 9.73 a | 10.83 a | 20.6 a | 0.19 a | 0.12 a |
| C - AI SY 0.25Z | 5.00 c | 9.87 a | 10.40 a | 20.3 a | 0.16 a | 0.10 a |
| D - AI SY 0.35Z 0.20T | 8.00 a | 8.53 ab | 11.07 a | 19.6 a | 0.19 a | 0.19 a |
| E - AI SY 0.25Z 0.20T | 8.67 a | 9.00 ab | 11.57 a | 20.6 a | 0.16 a | 0.26 a |

The two groups treated with talc (D, E) showed significantly better quality than any of the other groups, including a significant difference from group C, the group treated with an active ingredient and a superabsorbent polymer, but no talc. In particular, the significant variation in quality between group C and group E (which only vary with respect to the addition of talc) may suggest that talc has benefits beyond increasing the flowability of seeds.

Furthermore, as reflected in all these tables, addition of a superabsorbent polymer significantly enhances a number of parameters of the seeds. Addition of a singulating substance does not appear to decrease the effect of the superabsorbent polymer while enhancing the flowability, and therefore the usability, of the seeds.

FIG. 6 is a graph comparing the amount of water in grams gained after a single saturation event and then subsequently lost by wheat seeds that are untreated (labeled I); treated only with Dividend Extreme at a rate of 2 fluid ounces per hundredweight (labeled H); treated with Dividend Extreme at a rate of 2 fluid ounces per hundredweight, a starch-g-poly (2-propenamide-co-2-propenoic acid) potassium salt starch graft copolymer at a 0.5% rate, and talc at a 0.2% rate (labeled G); and treated with Dividend Extreme at a rate of 2 fluid ounces per hundredweight, a starch-g-poly (2-propenamide-co-2-propenoic acid) potassium salt starch graft copolymer at a 1.0% rate, and talc at a 0.3% rate (labeled F). In this experiment, the single saturation event comprised treating an equal number of seeds with drops of water from a syringe, allowing the seeds to stand for 5 minutes, and draining the excess water via gravity at an angle of 45 degrees. This was conducted on a stainless-steel fine mesh screen at ambient lab conditions of temperature and relative humidity. From the graph, it appears that wheat seeds treated with an active ingredient, a superabsorbent polymer, and talc initially absorbed more than twice the amount of water as either untreated seeds or seeds treated with an active ingredient alone. It also appears that the superabsorbent polymer-treated seeds retained more water for a longer period of time than either the untreated seeds or the seeds treated with an active ingredient alone.

It will be obvious to those having skill in the art that many changes may be made to the details of the above-described embodiments. Furthermore, the methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified without departing from the scope of the invention as claimed hereinafter.

The invention claimed is:

1. A method for coating a seed with a superabsorbent polymer seed coating to produce a coated seed product, consisting essentially of:
    providing a plurality of seeds;
    applying an active ingredient to the seeds, wherein the active ingredient is selected from at least one of the following: nutrients, plant growth regulators, insecticides, fungicides, herbicides, and biological materials;
    applying a superabsorbent polymer to the seeds; to form a mixture of seeds, active ingredient, and superabsorbent polymer; and
    applying a singulating substance to the mixture, wherein the coated seed product is free of a binder or adhesive.

2. The method of claim 1, wherein the application of the singulating substance occurs after the addition of the superabsorbent polymer.

3. The method of claim 2, wherein the application of the singulating substance occurs within 5 seconds of the addition of the superabsorbent polymer.

4. The method of claim 2, wherein the application of the singulating substance occurs within 2 seconds of the addition of the superabsorbent polymer.

5. The method of claim 1, wherein the superabsorbent polymer is a starch-g-poly (2-propenamide-co-2-propenoic acid) potassium salt starch graft copolymer.

6. The method of claim 1, wherein the singulating substance is talc.

7. The method of claim 1, wherein the singulating substance is present at a rate of between about 0.05% and about 0.50% of the weight of the seed.

8. The method of claim 1, wherein the active ingredient is present at a rate of between about 0.01% and about 3.0% of the weight of the seed.

9. The method of claim 1, wherein the superabsorbent polymer is present at a rate of between about 0.10% and about 1.50% of the weight of the seed.

10. The method of claim 1, wherein the superabsorbent polymer is present at a rate of between about 0.2% and about 0.4% of the weight of the seed.

11. The method of claim 1, wherein the seed is selected from at least one of the following: corn, soybeans, wheat, cotton, sunflowers, sorghum, canola, vegetables, barley, oats and other small grains, dry beans, peas, lentils, and peanuts.

12. A method for coating a seed with a superabsorbent polymer seed coating to produce a coated seed product, comprising:
    providing a plurality of seeds;
    applying an active ingredient to the seeds, wherein the active ingredient is selected from at least one of the following: nutrients, plant growth regulators, insecticides, fungicides, herbicides, and biological materials;
    applying a superabsorbent polymer to the seeds; to form a mixture of seeds, active ingredient, and superabsorbent polymer; and
    applying a singulating substance to the mixture, wherein the coated seed product is free of a binder or adhesive.

* * * * *